US010617317B2

(12) United States Patent
Cohen et al.

(10) Patent No.: US 10,617,317 B2
(45) Date of Patent: Apr. 14, 2020

(54) HIGHLIGHTING AN ELECTRODE IMAGE ACCORDING TO AN ELECTRODE SIGNAL

(71) Applicant: Biosense Webster (Israel) Ltd., Yokneam (IL)

(72) Inventors: Benjamin Cohen, Haifa (IL); Ben Ami Novogrodsky, Haifa (IL); Natan Sharon Katz, Atlit (IL); Lior Zar, Poria Illit Israel (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 166 days.

(21) Appl. No.: 15/442,895

(22) Filed: Feb. 27, 2017

(65) Prior Publication Data
US 2018/0242868 A1    Aug. 30, 2018

(51) Int. Cl.
*A61B 5/04* (2006.01)
*A61B 5/044* (2006.01)
(Continued)

(52) U.S. Cl.
CPC .............. *A61B 5/044* (2013.01); *A61B 5/042* (2013.01); *A61B 5/0422* (2013.01); *A61B 5/0452* (2013.01); *A61B 5/062* (2013.01); *A61B 5/063* (2013.01); *A61B 5/068* (2013.01); *A61B 5/6852* (2013.01); *A61B 5/6869* (2013.01); *A61B 5/743* (2013.01); *A61B 18/1492* (2013.01); *A61B 5/6885* (2013.01); *A61B 5/6886* (2013.01);
(Continued)

(58) Field of Classification Search
None
See application file for complete search history.

(56) References Cited

U.S. PATENT DOCUMENTS 7,266,408 B2    9/2007    Bojovic et al.
8,369,921 B2    2/2013    Tegg et al.
(Continued)

FOREIGN PATENT DOCUMENTS

| EP | 2499968 A1 | 9/2012 |
| EP | 3092944 A1 | 11/2016 |
| EP | 3115011 A1 | 1/2017 |

OTHER PUBLICATIONS

Das, Moloy, et al., "Ablation index, a novel marker of ablation lesion quality: prediction of pulmonary vein reconnection at repeat electrophysiology study and regional differences in target values", Europspace, May 31, 2016, pp. 775-783.
(Continued)

*Primary Examiner* — Ankit D Tejani

(57) ABSTRACT

A method, consisting of presenting on a display screen a graphical image of a heart of a patient, including icons representing a catheter that is positioned within the heart and an electrode on the catheter, while the electrode is in contact with tissue at a location in the heart. The method further includes acquiring, using the electrode, electrical signals from the tissue at the location, and processing the acquired signals so as to detect an occurrence of a predefined signal feature in the acquired signals. The method also includes, upon detecting the occurrence of the predefined signal feature, modifying a visual feature of at least one of the icon representing the electrode and the icon representing the catheter on the display screen.

34 Claims, 6 Drawing Sheets

(51) Int. Cl.
  *A61B 5/00* (2006.01)
  *A61B 5/0452* (2006.01)
  *A61B 5/042* (2006.01)
  *A61B 5/06* (2006.01)
  *A61B 18/14* (2006.01)
  *A61B 18/00* (2006.01)

(52) U.S. Cl.
  CPC .............. *A61B 2018/00351* (2013.01); *A61B 2018/00577* (2013.01); *A61B 2505/05* (2013.01)

(56) References Cited

U.S. PATENT DOCUMENTS

| | | |
|---|---|---|
| 8,388,547 B2 | 3/2013 | Revishvili et al. |
| 8,456,182 B2 | 6/2013 | Bar-Tal et al. |
| 8,529,461 B2 | 9/2013 | Revishvili et al. |
| 8,838,216 B2 | 9/2014 | Francis et al. |
| 8,849,389 B2 | 9/2014 | Ramanathan et al. |
| 10,517,670 B2 | 12/2019 | Bar-Tal |
| 2009/0171321 A1 | 7/2009 | Callaghan |
| 2009/0177111 A1 | 7/2009 | Miller et al. |
| 2010/0168729 A1 | 7/2010 | Wang et al. |
| 2012/0237093 A1* | 9/2012 | Turgeman ............ A61B 5/0422 382/128 |
| 2015/0119738 A1 | 4/2015 | Deno |
| 2016/0183824 A1 | 6/2016 | Severino |

OTHER PUBLICATIONS

Extended European Search Report for corresponding European patent application EP 18158512.6, dated Jun. 18, 2018.

* cited by examiner

HIGHLIGHTING AN ELECTRODE IMAGE ACCORDING TO AN ELECTRODE SIGNAL

FIELD OF THE INVENTION

The present invention relates generally to cardiac surgery, and specifically to presentation of an image related to signals acquired during the surgery.

BACKGROUND OF THE INVENTION

During an invasive medical procedure, many parameters must be monitored simultaneously by the professional performing the procedure. There are a number of aids to such monitoring.

For example, U. S. Patent Application 2009/0111321 to Callaghan, whose disclosure is incorporated herein by reference, describes an image acquisition device which is configured to obtain real-time two-dimensional images of a portion of a patient's body that is disposed within the field of view of the image acquisition device. A workstation is configured to integrate and register a three-dimensional model of an anatomic structure with the two-dimensional image.

U. S. Patent Application 2010/0168729 to Wang et al., whose disclosure is incorporated herein by reference, describes how an electrophysiological (EP) monitor or display such as an electrogram signal display, may be integrated into an ablation electrode assembly.

U.S. Pat. No. 7,266,408 to Bojovic et al., whose disclosure is incorporated herein by reference, describes a three-dimensional presentation of the human heart that may be correlated with waveforms specific for standard ECG or derived ECG signals based on the dipole approximation of the heart electrical activity. The three-dimensional heart model may be rotated, and the ECG signals are interactively linked to the model.

U. S. Patent Application 2016/0183824 to Severino, whose disclosure is incorporated herein by reference, describes a system for visualization of electrophysiology information sensed by electrodes on a catheter. The system includes recording times of electrode signal acquisition and designating a reference electrode signal acquisition.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

presenting on a display screen a graphical image of a heart of a patient, including icons representing a catheter that is positioned within the heart and an electrode on the catheter, while the electrode is in contact with tissue at a location in the heart;

acquiring, using the electrode, electrical signals from the tissue at the location;

processing the acquired signals so as to detect an occurrence of a predefined signal feature in the acquired signals; and upon detecting the occurrence of the predefined signal feature, modifying a visual feature of at least one of the icon representing the electrode and the icon representing the catheter on the display screen.

In a disclosed embodiment the predefined signal feature includes a morphological feature of the signal.

In a further disclosed embodiment the predefined signal feature includes a temporal feature of the signal.

Typically, modifying the visual feature includes modifying the visual feature only while the occurrence of the predefined signal feature is detected. Alternatively, modifying the visual feature includes modifying the visual feature for a preset time period from detection of the occurrence of the predefined signal feature.

In an alternative embodiment the electrical signals include electropotentials generated by the tissue.

Alternatively or additionally the electrical signals include signals generated by externally applied currents flowing between the electrode and skin of the patient. The predefined signal feature may consist of a confidence metric for the electrode touching the tissue of the heart. Alternatively, the predefined signal feature may consist of an ablation index representative of a size of a lesion, in the tissue, produced by the externally applied currents ablating the tissue.

There is further provided, according to an embodiment of the present invention, apparatus, including:

a catheter;

an electrode positioned on the catheter;

a display screen upon which is presented a graphical image of a heart of a patient, including icons representing the catheter that is positioned within the heart and the electrode, while the electrode is in contact with tissue at a location in the heart; and a processor, configured to:

acquire, using the electrode, electrical signals from the tissue at the location, process the acquired signals so as to detect an occurrence of a predefined signal feature in the acquired signals, and upon detecting the occurrence of the predefined signal feature, modify a visual feature of at least one of the icon representing the electrode and the icon representing the catheter on the display screen.

The present disclosure will be more fully understood from the following detailed description of the embodiments thereof, taken together with the drawings, in which:

DETAILED DESCRIPTION OF EMBODIMENTS

Overview

Figure 1:
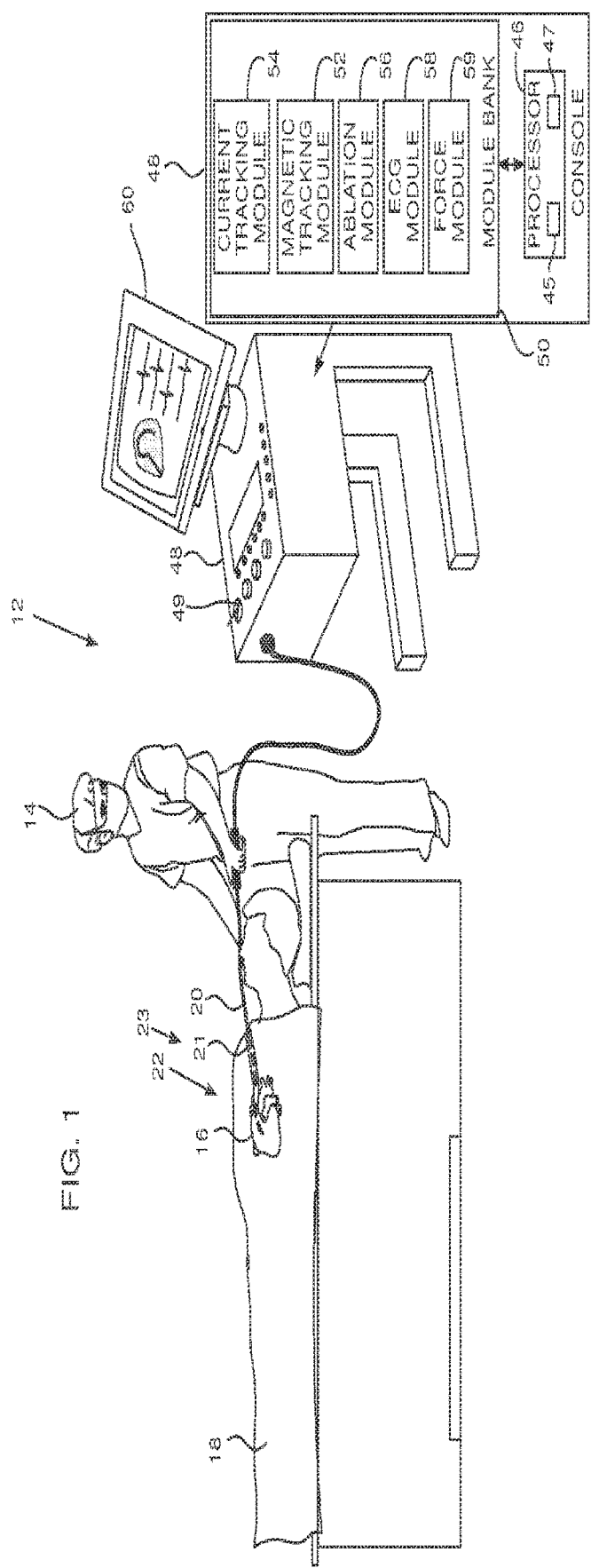
FIG. 1 is a schematic illustration of an invasive medical procedure, according to an embodiment of the present invention.

Embodiments of the present invention provide an aid to a professional performing an invasive cardiac procedure, so as to improve the tracking of events occurring during the procedure.

A graphical image of the heart of the patient upon which the procedure is being performed is presented on a display screen. The image includes icons representing a catheter and associated electrodes that the professional has positioned in the patient's heart, so that the electrodes typically contact tissue at respective locations in the heart.

The electrodes acquire electrical signals from the tissue at the location, and a processor processes the signals so as to detect an occurrence of a predefined signal feature in the acquired signals. A typical predefined signal feature is the occurrence of multiple potential maxima within a time window of interest that may be defined by the professional.

Upon detection of the occurrence of the predefined signal feature in the signal from one of the electrodes, the processor may modify a visual feature of the icon representing that electrode. A typical modification comprises changing the color of the electrode icon. Alternatively or additionally, for example if the predefined signal feature occurs in two adjacent electrodes, the icon representing the catheter between the electrodes may be modified visually, for example by changing the color of that portion of the catheter icon.

By providing the visual modification to the electrode and/or catheter icon, the professional is relieved of the necessity of looking, at substantially the same time, at both the electrical signal and at the catheter and electrode icons.

System Description

In the following description, like elements in the drawings are identified by like numerals, and the like elements are differentiated as necessary by appending a letter to the identifying numeral.

FIG. 1 is a schematic illustration of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue or on non-biological material.

In order to perform the ablation, professional 14 inserts a probe 20 into a sheath 21 that has been pre-positioned in a lumen of the patient. Sheath 21 is positioned so that a distal end 22 of the probe may enter the heart of the patient, after exiting a distal end 23 of the sheath, and contact tissue of the heart.

Probe 20 may comprise any type of catheter that can be inserted into the heart of the patient, and that can be tracked using a magnetic tracking system and/or an impedance measuring system, both of which systems are described further below. For example, probe 20 may comprise a lasso catheter, a shaft-like catheter, or a pentarray catheter, produced by Biosense Webster of Diamond Bar, Calif., or catheters generally similar to these catheters. In order to be tracked by the magnetic tracking system the probe has at least one magnetic sensor, and in order to be tracked by the impedance measuring system the probe has at least one electrode.

For clarity and simplicity, in the following description probe 20 is assumed to comprise a lasso catheter, with multiple electrodes and one or more magnetic sensors at its distal end 22, as is described below with reference to FIG. 2. Those having ordinary skill in the art will be able to adapt the description, mutatis mutandis, for probes having only magnetic sensors, probes having only electrodes, and probes having combinations of magnetic sensors and electrodes other than that exemplified here, and all such probes are assumed to be comprised within the scope of the present invention.

Figure 2:
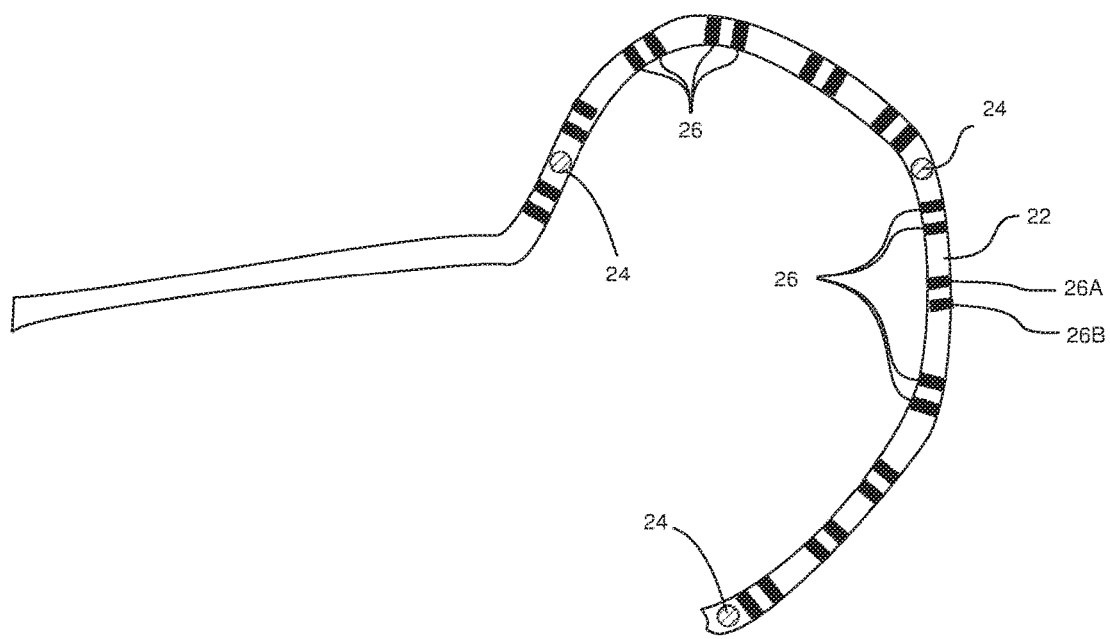
FIG. 2 is a schematic diagram of a distal end of a probe, according to an embodiment of the present invention.

FIG. 2 is a schematic diagram of distal end 22, according to an embodiment of the present invention. Distal end 22 comprises a plurality of electrodes 26, typically grouped in pairs on the distal end. As is explained below, the electrodes may be used for acquiring electropotential (EP) signals from myocardium 16, for pacing, i.e., injecting signals into the myocardium, for ablating the myocardium, and also as transfer electrodes for current used to determine the location of the electrodes. It will be understood that all of these functions may be implemented sequentially or simultaneously, and that if they are implemented simultaneously, the different signals, because they are in different frequency bands, may be separated by appropriate filtering.

Distal end 22 also comprises one or more magnetic field sensors 24. Sensors 24 are typically single axis sensors (SASs) or triple axis sensors (TASs), both of which are well known in the art.

Returning to FIG. 1, apparatus 12 is controlled by a system processor 46 which comprises real-time noise reduction circuitry 45, typically configured as a field programmable gate array (FPGA), followed by an analog-to-digital (A/D) ECG (electrocardiograph) signal conversion integrated circuit 47. The processor can pass the signal from A/D ECG circuit 47 to another processor and/or can be programmed to perform at least one algorithm disclosed herein, the algorithm comprising steps described hereinbelow. The processor uses circuitry 45 and circuit 47, as well as features of modules which are described in more detail below, in order to perform the algorithm.

Processor 46 is located in an operating console 48 of the apparatus. Console 48 comprises controls 49 which are used by professional 14 to communicate with the processor. During the procedure, processor 46 communicates with a magnetic tracking module 52 and a current tracking module 54 in a module bank 50, in order to track locations and orientations of elements of the probe.

Module 52 enables the processor to use a magnetic tracking method, wherein magnetic transmitters external to patient 18 generate signals in sensors 24. The signals generated by the sensors, in response to magnetic fields from the transmitters that traverse the sensors, allow the sensors to act as location and orientation detectors for the elements of the probe, in this case in the distal end, where the sensors are situated. The Carto® system produced by Biosense Webster, of Diamond Bar, Calif., uses such a tracking method.

Module 54 enables the processor to use a current tracking method, which measures externally applied currents flowing between electrodes 26 of the probe and electrodes on the skin of patient 18. The processor and module 54 use the measured currents, or corresponding impedances, to generate coordinates of locations of elements of the probe where the electrodes are situated. U.S. Pat. No. 8,456,182, to Bar-Tal et al., which is incorporated herein by reference, describes such a current tracking method. (The Carto® system also uses such a current tracking method.) Module bank 50 also comprises an ablation module 56, an ECG (electrocardiogram) module 58, and a force module 59. Ablation module 56 enables processor 46 to inject radiofrequency (RF) current, via selected electrodes 26 of the probe and returning electrodes on the skin of the patient, into myocardium 16, in order to ablate regions of the myocardium which are in contact with the selected electrodes. The ablation module also enables the processor to set parameters of the injected current, such as its frequency, the power dissipated, and the duration of the injection.

ECG module 58 enables processor 46 to acquire and analyze EP signals received by electrodes 26. As is described in more detail below, the signals are typically presented to professional 14 as voltage-time graphs which are updated in real time. As is also described in more detail below, the ECG module analyzes the EP signals so as to enable processor 46 to identify features of the acquired signals.

Force module 59 enables processor 46 to measure the contact force on distal end 22.

The software for processor 46 and module bank 50 may be downloaded to the processor in electronic form, over a network, for example. Alternatively or additionally, the software may be provided on non-transitory tangible media, such as optical, magnetic, or electronic storage media.

In order to operate apparatus 12, module bank 50 typically comprises modules other than those described above, such an irrigation module allowing the processor to control irrigation provided for the distal end. For simplicity, such other modules are not illustrated in FIG. 1. All modules may comprise hardware as well as software elements.

Results of the procedure may be presented on a display screen 60, as is described below with reference to FIG. 3.

Figure 3:
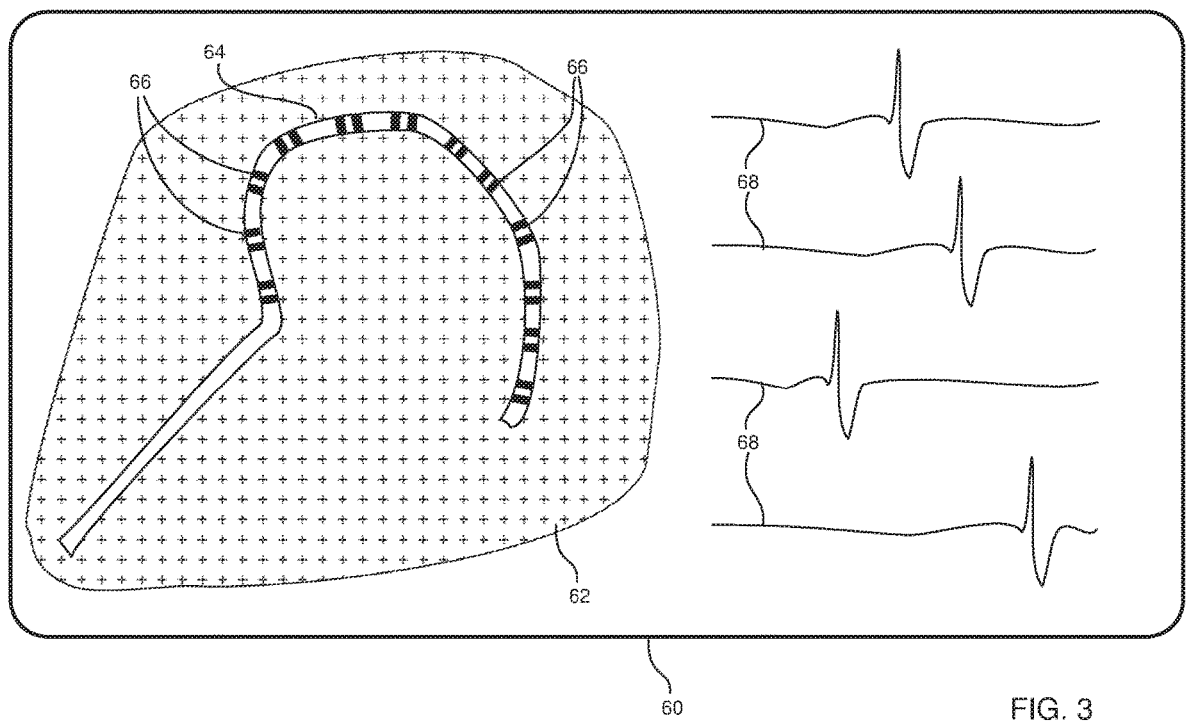
FIG. 3 is a schematic diagram of a display screen, according to an embodiment of the present invention.

FIG. 3 is a schematic diagram of display screen 60, according to an embodiment of the present invention. During the procedure, a graphical image 62, typically a three-dimensional (3D) image of a portion of the heart of patient 18, is presented on a first part of screen 60. Typically, the 3D image is generated by mapping points in the heart with a tracking catheter, and converting the mapped points to a 3D surface, by methods which are well known in the art.

Overlaid on image 62 is an icon 64 of distal end 22 of the lasso catheter, and on icon 64 are respective representative icons 66 of electrodes 26.

As stated above, ECG module 58 enables processor 46 to acquire EP signals from electrodes 26, and during the procedure, the processor presents the signals on a second part of screen 60. The signals are presented as voltage vs. time graphs 68. Typically, if the signals are presented as unipolar signals, there is a graph 68 for each electrode 26. Alternatively, if the signals are presented as bipolar signals, there is a graph 68 for each pair of electrodes 26. For clarity and simplicity, only four graphs 68 are shown in FIG. 3.

During the procedure, the algorithm of processor 46 uses current tracking module 54 to inject currents via electrodes 26 into patient 18. From the impedances presented to the injected currents, the processor is able to estimate the position of each of electrodes 26 conveying the currents. Alternatively or additionally, the processor uses magnetic tracking module 52 to analyze signals received from sensors 24, so as to determine the orientation and location of the sensors.

While the position of heart portion image 62 may be kept fixed on screen 60, the position and orientation of distal end icon 64, and of electrode icons 66, are typically updated in real time on screen 60, as they are overlaid on image 62. In addition graphs 68, of the EP signals acquired from electrodes 26 by ECG module 58, are also typically updated in real time.

Figure 4:
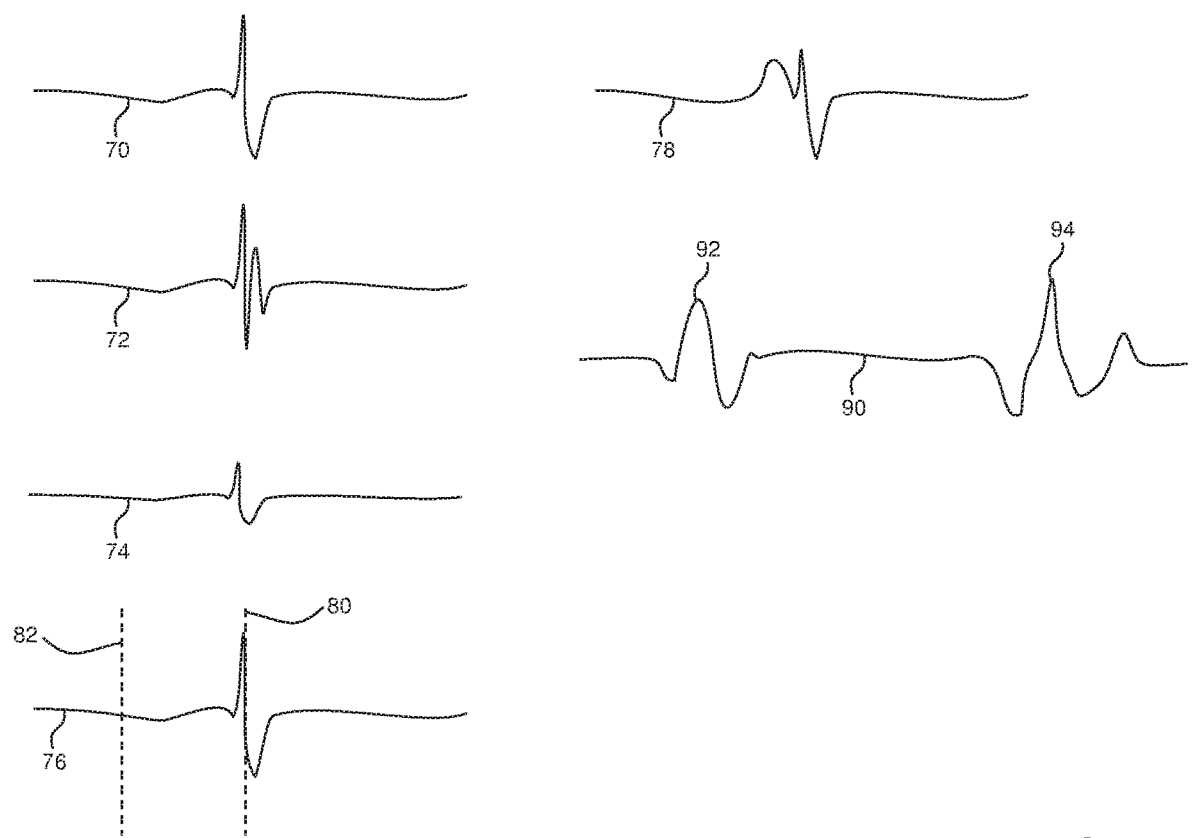
FIG. 4 illustrates electrophysiological signals that are classified by a processor, according to an embodiment of the present invention.

FIG. 4 illustrates EP signals that are classified by the algorithm of processor 46 using ECG module 58, according to an embodiment of the present invention. Module 58 analyzes, in real time, the incoming signals acquired from each electrode 26. The analysis includes measuring potential amplitudes V(t) at times t, and evaluating values of the first time derivative $$\frac{dV(t)}{dt}$$

and the second time derivative $$\frac{d^2V(t)}{dt^2},$$

typically after filtering the signals to remove noise an baseline drift. From the time and the measured values of the potentials and the first and second derivatives, processor 46 is able to identify one or more features in the signal that characterize the signal acquired from each electrode 26 morphologically, i.e., in terms of the signal shape. Alternatively or additionally, the processor is able to identify one or more features in the signal that characterize the signal acquired from each electrode 26 temporally, i.e., in terms of one or more times of occurrence of respective defined aspects of the signal. The identified features enable the processor to assign the signal to a particular type or classification.

Table I below provides examples of different signal types of EP signals that the processor is able to classify morphologically and/or temporally, and respective identifying features that the processor uses to generate the classification. The table lists a schematic graph illustrating the signal type.

TABLE I

| Signal Type | Identifying Features | Schematic V vs. t Graph |
| --- | --- | --- |
| Normal sinus rhythm signal (Activation width) | A time width of an intra-cardiac activation. In one embodiment the time width is greater than 0.02 s. | Graph 70 |
| Normal sinus rhythm signal (Unipolar/Bipolar correlation) | The correlation coefficient between a calculated bipolar peak signal value compared to the two corresponding calculated unipolar signal values. In one embodiment the correlation coefficient is greater than 0.8. | Graph 70 |
| Complex signal | Multiple, i.e., two or more, peaks above a predefined threshold and within a predefined window of interest around a reference annotation. In a disclosed embodiment the threshold is 1.5 µV and the window of interest is 0.4 s. | Graph 72 |
| Reduced signal | The ratio between a pre-recorded local maximum voltage in a window of interest (WOI) and the local maximum voltage in the WOI of the current signal. In one embodiment the ratio is less than 0.3. | Graph 74 |
| Signal to be matched with a pattern | The correlation coefficient between a predefined recorded signal and the real-time received signal. In one embodiment | Graph 78 |

TABLE I-continued

| Signal Type | Identifying Features | Schematic V vs. t Graph |
|---|---|---|
| Signal used to measure conduction velocity | the correlation coefficient is greater than 0.9. The value of the downward slope during activation. In one embodiment the absolute slope is less than 1 mV/s. | Graph 78 |
| Time related signal | Time of occurrence of a defined aspect of the signal. | Graph 76 |
| Signal showing atrial and ventricle activation | The time between the atrial activation and the ventricle activation. In one embodiment the time is less than 100 ms | Graph 90 |

In the case of a time related signal, illustrated by graph 76, a time of occurrence 80 of the signal typically corresponds to a local activation time (LAT) of the signal. Time of occurrence 80 is usually measured with respect to a reference time 82, typically a time generated by a reference signal acquired from a reference electrode.

The case of a signal showing atrial and ventricle activation is illustrated by graph 90. A signal 92 corresponds to atrial activation, and a signal 94 corresponds to ventricle activation. A time between the two signals depends on the position of the electrode 26 detecting activations within the heart, and is typically in the range of 100-600 ms.

In addition to analyzing EP signals from each electrode 26, processor 46 is able to analyze other non-EP signals from the electrodes, such as the currents and powers dissipated through the electrodes that are measured by current tracking module 54 and/or ablation module 56. Also from this analysis, processor 46 is able to identify one or more features that characterize the non-EP signals.

Table II below provides examples of non-EP signals associated with an electrode, and respective identifying features that the processor uses to characterize the signals.

TABLE II

| Signal Type | Identifying Feature |
|---|---|
| Current | Current through the electrode is used to measure impedance seen by the electrode. Impedance is used as a confidence metric for the electrode touching tissue. In one embodiment the impedance is less than 100 Ω. |
| Power | For an electrode used to ablate tissue, the power through the electrode is used, together with other parameters associated with the electrode, to measure an ablation index associated with the electrode. An ablation index, described in more detail below, is a parameter providing a measure of the size of a lesion produced in the tissue by the power dissipated at the electrode. In one embodiment the ablation index is greater than 5 mm. |

The algorithm according to the present invention uses an ablation index that is a function, having a value that changes as ablation proceeds, which provides an estimate of the size of a lesion produced by the ablation of a tissue of known type. The estimate provided by the index depends on the values of the contact force CF and power P measured during the ablation, as well as on the period of time of the ablation.

Ablation indices are described in an article entitled "Ablation Index-guided Pulmonary Vein Isolation for Atrial Fibrillation may Improve Clinical Outcomes in Comparison to Contact Force-guided Ablation" to Hussein et al., presented at the 2016 Heart Rhythm Congress, and in U.S. Patent Application 2017/0014181 to Bar-Tal et al. Both documents are incorporated herein by reference.

Equation (1) below gives an expression for an ablation index:

$$D = (C\int_0^t CF^\alpha(\tau) P^\beta(\tau) d\tau)^\delta = \text{Ablation Index} \quad (1)$$

where C is a constant having a value depending on the type of tissue being ablated; in one embodiment C has an approximate value of 0.002, α is an exponent having a value typically in the range 0.6-0.8, β is an exponent having a value typically in the range 1.4-1.8, δ is an exponent having an approximate value of 0.35, and D is an estimate of the depth of a lesion achieved by ablating for a time t, with instantaneous contact force CF(τ) and instantaneous power P(τ), and where τ represents a time variable. Instantaneous contact force CF(τ) is measured by force module 59; instantaneous power P(τ) is measured by ablation module 56.

Figure 5:
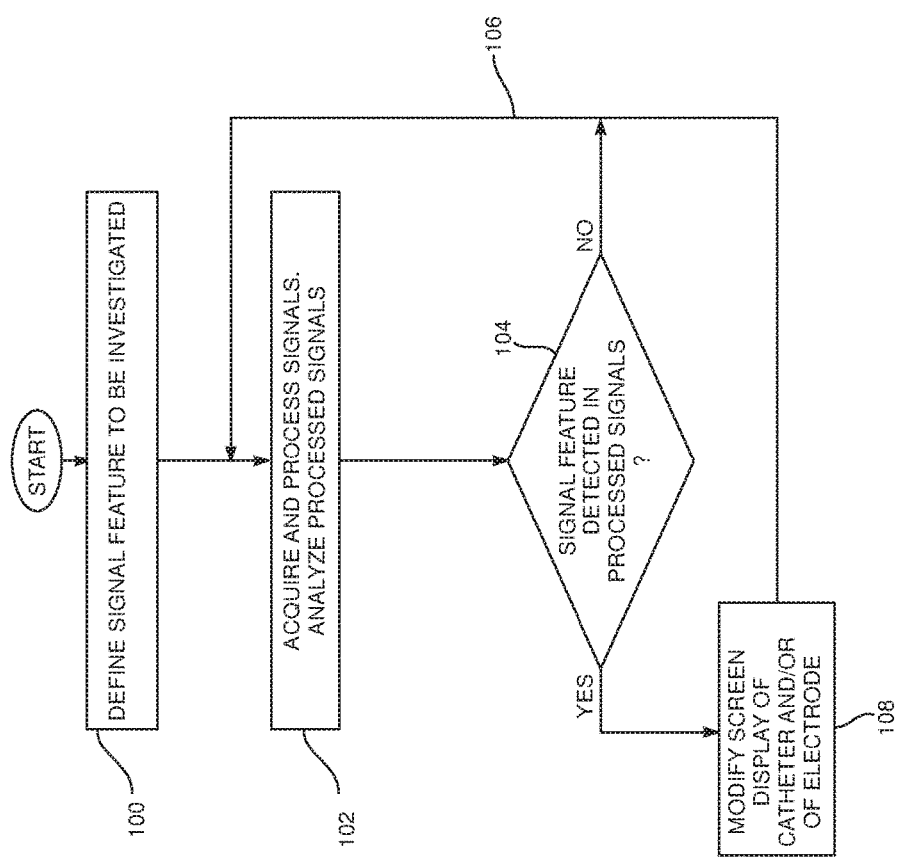
FIG. 5 is a flowchart of steps performed by the processor, according to an embodiment of the present invention.
Figure 6:
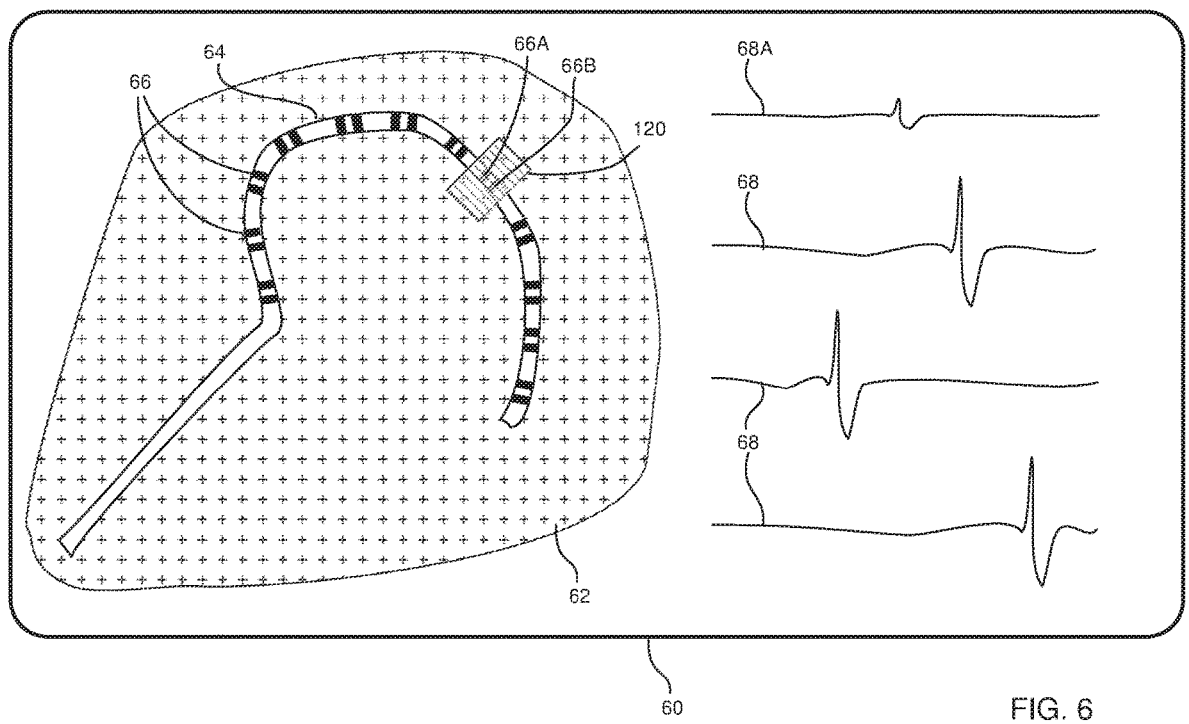
FIG. 6 illustrates one of the steps of the flowchart, according to an embodiment of the present invention

FIG. 5 is a flowchart of steps of the algorithm performed by processor 46 and professional 14 in operating apparatus 12, and FIG. 6 illustrates one of the steps of the flowchart, according to an embodiment of the present invention. The steps of the algorithm depicted in the flowchart describe conditions for modifying the distal end icon 64 and/or one or more electrode icons 66 on screen 60 while apparatus 12 is operating. For clarity and simplicity, except where otherwise stated, the description of the flowchart assumes that signals analyzed by processor 46 are EP signals. Those having ordinary skill in the art will be able to adapt the description, mutatis mutandis, for the acquisition of non-EP signals.

In an initial setup step 100 professional 14 selects a signal type, as exemplified in Table I and Table II, to be investigated, and processor 46 registers the identifying feature or features of the selected signal type. Alternatively, professional 14 may provide the identifying feature or features directly to the processor. Examples of typical identifying features are provided in Tables I and II, and those having ordinary skill in the art will be able to formulate other identifying features.

The selection of the signal type, or the selection and provision of the identifying features, are typically via a selection menu provided to professional 14 on screen 60, and the professional uses controls 49 to choose a desired type or feature from the menu.

In some embodiments, a plurality of signal types may be selected in step 100; for example, the signal type selected may include a complex signal and a reduced signal. In a disclosed embodiment, the signal type may exclude one or more signal types; for example, the signal type selected may include all types other than a normal sinus rhythm type.

In a signal acquisition step 102, the processor acquires respective appropriate signals from each electrode 26, and for EP signals processes each of the signals to remove noise and baseline drift. For the acquisition of EP signals the processor typically measures and stores the values V(t) at time t of each signal, as well as the first and second derivatives of each signal. The acquisition and processing is typically performed on a continuous basis, in real time, as signals continue to be acquired by electrodes 26.

The processor analyzes the processed signals, typically, for EP signals by operating on a windowed section of the processed signals, in order to identify the one or more signal features defined in step 100.

In a decision step 104, the processor inspects each of the respective signals acquired from electrodes 26 for the signal feature or features defined in setup step 100. If the feature or features are not found in any of the acquired signals, the flowchart returns to step 102, as illustrated by an arrow 106.

If the feature or features are found in one or more of the acquired signals, then in a screen modification step 108 a visual feature of icons 64 and/or 66, i.e., the icons representing distal end 22 and electrodes 26, is modified. The modification may comprise any convenient modification, such as changing a color or shade of the icon, increasing or reducing a size of the icon, and/or surrounding and/or covering the icon by another icon.

After the modification performed in step 108, the flowchart returns to step 102.

The features identified in step 104 may typically be transient features, so that they do not repeat continuously. In this case the visual feature modification performed in step 108 is also typically transient, so that the modification implemented on screen 60 appears as a "flash" for a transient period of approximately one second, after which the screen display returns to its unmodified state. However, in some embodiments, in the initial setup step 100, a preset time period greater than the transient period, selected by professional 14, may be applied for the modification of step 108, so that the modification persists for the preset period before the screen display returns to its unmodified state.

FIG. 6 illustrates step 108, wherein, by way of example, in the initial setup of the flowchart of FIG. 5 the signal type is selected as a reduced signal described above in Table I. E.g., the signal features the processor determines in decision step 104 typically correspond to those of an intracardiac-during-ablation signal, but with a reduced amplitude compared to the normal intracardiac pre-ablation signal.

A signal 68A is acquired from electrodes 26A, 26B (FIG. 2) and in step 104 the processor returns a positive value, since the signal corresponds to a reduced amplitude normal sinus signal. In this case in step 108 the processor modifies the screen display by overlaying the icons of electrodes 26A, 26B, i.e. electrode icons 68A, 68B, with a partially transparent shaded rectangle 120, the rectangle indicating that electrodes 26A and 26B are the source of reduced amplitude normal sinus signal 68A.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
   presenting on a display screen a graphical image of a heart of a patient, including icons representing a catheter that is positioned within the heart and icons representing one or more electrodes on the distal end of the represented catheter, while the one or more electrodes are in contact with tissue at a location in the heart and presenting on the display screen voltage versus time graphs of the one or more electrodes;
   providing at least two different predefined signal types, each such signal type based on different potential amplitudes and times;
   selecting at least one such predefined signal type to be investigated from the at least two different predefined signal types;
   acquiring, using one or more of the electrodes, one or more electrical signals from the tissue at the location;
   processing the acquired signal so as to detect an occurrence of the selected predefined signal type in the acquired signal; and
   upon detecting the occurrence of the selected predefined signal type, modifying a visual feature of at least one of the icons on the distal end of the represented catheter representing the at least one or more electrodes on the display screen.

2. The method according to claim 1, wherein the selected predefined signal type comprises a morphological feature of the signal.

3. The method according to claim 1, wherein the selected predefined signal type comprises a temporal feature of the signal.

4. The method according to claim 1, wherein modifying the visual feature comprises modifying the visual feature only while the occurrence of the selected predefined signal type is detected.

5. The method according to claim 1, wherein modifying the visual feature comprises modifying the visual feature for a preset time period from detection of the occurrence of the selected predefined signal type.

6. The method according to claim 1 wherein the electrical signals comprise electropotentials generated by the tissue.

7. The method according to claim 1 wherein the electrical signals comprise signals generated by externally applied currents flowing between the one or more electrodes and skin of the patient.

8. The method according to claim 7, wherein the selected predefined signal type comprises a confidence metric for the electrode touching the tissue of the heart.

9. The method according to claim 7, wherein the selected predefined signal type comprises an ablation index representative of a size of a lesion, in the tissue, produced by the externally applied currents ablating the tissue.

10. The method according to claim 1, wherein the electrical signal is a normal sinus rhythm signal.

11. The method according to claim 1, wherein the electrical signal is a complex signal.

12. The method according to claim 1, wherein the electrical signal is a reduced signal.

13. The method according to claim 1, wherein the electrical signal is a signal to be matched with a pattern.

14. The method according to claim 13, wherein the electrical signal is a time related signal.

15. The method according to claim 13, wherein the electrical signal is a signal showing atrial and ventrical activation.

16. The method according to claim 13, wherein the electrical signal is current.

17. The method according to claim 13, wherein the electrical signal is power.

18. Apparatus, comprising:
   a catheter;
   one or more pair of electrodes positioned on the distal end of the catheter;
   a display screen upon which is presented a graphical image of a heart of a patient, including icons representing the catheter that is positioned within the heart and located on a distal and of the represented catheter icons representing one or more electrodes, while the one or more electrodes are in contact with tissue at a location in the heart and upon which is presented on the display screen voltage versus time graphs of the one or more electrodes; and a processor, configured to:

provide at least two different predefined signal types, each of such signal type based on different potential amplitudes and time;

selecting at least one such predefined signal type to be investigated from the at least two different predefined signal types;

acquire, using the one or more electrodes, one or more electrical signals from the tissue at the location, process the acquired signal so as to detect an occurrence of the selected predefined signal type in the acquired signals, and upon detecting the occurrence of the selected predefined signal type, modify a visual feature of at least one of the icons on the distal end of the catheter representing one or more of the electrodes on the display screen.

19. The apparatus according to claim 18, wherein the selected predefined signal type comprises a morphological feature of the signal.

20. The apparatus according to claim 18, wherein the selected predefined signal type comprises a temporal feature of the signal.

21. The apparatus according to claim 18, wherein modifying the visual feature comprises modifying the visual feature only while the occurrence of the selected predefined signal type is detected.

22. The apparatus according to claim 18, wherein modifying the visual feature comprises modifying the visual feature for a preset time period from detection of the occurrence of the selected predefined signal type.

23. The apparatus according to claim 18, wherein the electrical signals comprise electropotentials generated by the tissue.

24. The apparatus according to claim 18, wherein the electrical signals comprise signals generated by externally applied currents flowing between the one or more electrodes and skin of the patient.

25. The apparatus according to claim 24, wherein the selected predefined signal feature comprises a value of a confidence metric for the one or more electrodes touching the tissue of the heart.

26. The apparatus according to claim 24, wherein the selected predefined signal type comprises a value of an ablation index representative of a size of a lesion, in the tissue, produced by the externally applied currents ablating the tissue.

27. The apparatus according to claim 18, wherein the electrical signal is a normal sinus rhythm signal.

28. The apparatus according to claim 18, wherein the electrical signal is a complex signal.

29. The apparatus according to claim 18, wherein the electrical signal is a reduced signal.

30. The apparatus according to claim 18, wherein the electrical signal is a signal to be matched with a pattern.

31. The apparatus according to claim 18, wherein the electrical signal is a time related signal.

32. The apparatus according to claim 18, wherein the electrical signal is a signal showing atrial and ventrical activation.

33. The apparatus according to claim 18, wherein the electrical signal is current.

34. The apparatus according to claim 18, wherein the electrical signal is power.

* * * * *